US006423847B1

(12) United States Patent
Pearson et al.

(10) Patent No.: US 6,423,847 B1
(45) Date of Patent: Jul. 23, 2002

(54) SYNTHESIS AND CLINICAL USES OF D,α-TOCOPHEROL NICOTINATE COMPOUNDS

(75) Inventors: Don C. Pearson, Lakewood, WA (US); Kenneth T. Richardson, Anchorage, AK (US)

(73) Assignee: Chronorx, LLC, Anchorage, AK (US)

( * ) Notice: Subject to any disclaimer, the term of this patent is extended or adjusted under 35 U.S.C. 154(b) by 0 days.

(21) Appl. No.: 09/532,658

(22) Filed: Mar. 20, 2000

Related U.S. Application Data

(60) Provisional application No. 60/128,154, filed on Apr. 7, 1999.

(51) Int. Cl.$^7$ ........................ C07D 405/00; A61K 31/44
(52) U.S. Cl. ..................................... 546/282.7; 514/337
(58) Field of Search ........................ 546/282.7; 514/337

(56) References Cited

FOREIGN PATENT DOCUMENTS

ES            310746         *   8/1973

OTHER PUBLICATIONS

CA 118:116453, "Vitamin E binds to specific binding sites and enhances prostacyclin production by cultured aortic endothelial cells", Throm. Baemostasis (1992), 68 (6), 744–51.*
Chung et. al., "Reducing Lipid Peroxidation Stress of Erythrocyte Membrane by alpha–Tocopherol Nicotinate Plays an Important Role in Improving Blood Rheological Propertiews in Type 2 Diabetic Patients with Retinophathy", Diabetic Medicine, vol. 15, pages, 1998.*
CA reference 118:116453, "Vitamin E binds to specific binding sites and enhances prostacyclin production by cultured aortic endothelial cells", Thromb. Haemostasis (1992), 68(6), 744–51.*
Agte, V. V., K. M. Paknikar, et al. (1997). "Effect of nicotinic acid on zinc and iron metabolism." *Biometals* 10(4): 271–6.
Boger, R. H., S. M. Bode–Boger, et al. (1998). "Dietary L–arginine and alpha–tocopherol reduce vascular oxidative stress and preserve endothelial function in hypercholesterolemic rabbits via different mechanisms [In Process Citation]." *Atherosclerosis* 141(1):31–43.
Chung, T. W., J. J. Yu, et al. (1998). "Reducing lipid peroxidation stress of erythrocyte membrane by alpha–tocopherol nicotinate plays an important role in improving blood rheological properties in type 2 diabetic patients with retinopathy." *Diabet Med* 15(5):380–5.
Ghung, T. W., J. J. Yu, et al. (1998). "Reducing lipid peroxidation stress of erythrocyte membrane by alpha–tocopherol nicotinate plays an important role in improving blood rheological properties in type 2 diabetic patients with retinopathy." *Diabet Med* 15(5):380–5.
Johansson, J. O., N. Egberg, et al. (1997). "Nicotinic acid treatment shifts the fibrinolytic balance favourably and decreases plasma fibrinogen in hypertriglyceridaemic men [see comments]." *J Cardiovasc Risk* 4(3):165–71.
Li, R. K., D. B. Cowan, et al. (1996). "Effect of vitamin E on human glutathione peroxidase (GSH–PX1) expression in cardiomyocytes." *Free Radic Biol Med* 21(4):419–26.
Neuzil, J., S. R. Thomas, et al. (1997). "Requirement for, promotion, or inhibition by alpha–tocopherol of radical–induced initiation of plasma lipoprotein lipid peroxidation." *Free Radic Biol Med* 22(1–2): 57–71.
Philip, C. S., L. A. Cisar, et al. (1998). "Effect of niacin supplementation on fibrinogen levels in patients with peripheral vascular disease." *Am J Cardiol* 82(5):697–9, A9.

* cited by examiner

*Primary Examiner*—Alan L. Rotman
*Assistant Examiner*—Binta Robinson
(74) *Attorney, Agent, or Firm*—Townsend and Townsend and Crew, LLP

(57) ABSTRACT

A process of synthesis of D,α-tocopherol nicotinate compounds is presented. Therapeutic uses for this compound are described. The active agents are demonstrated to be complementary in their physiological functions especially as these relate to cellular and endothelial biochemistry and physiology and, ultimately to vascular health. The active components of the invention are selected for inclusion in a unique combination that clinically reduces risks of vasculopathy, DNA strand breakage and neuronal excitotoxicity in various diseases. In addition to the systemic vascular benefits acquired, improvement of the vascular health of the eye reduces the risk of glaucomatous optic nerve atrophy with its accompanying visual field loss and potential blindness and reduces conditions of risk for macular degeneration.

1 Claim, No Drawings

SYNTHESIS AND CLINICAL USES OF D,α-TOCOPHEROL NICOTINATE COMPOUNDS

CROSS REFERENCE TO RELATED APPLICATION

This application is related to United States Provisional Patent Application No. 60/128,154, filed Apr. 7, 1999, and claims all benefits legally available therefrom. Provisional Patent Application No. 60/128,154 is hereby incorporated by reference for all purposes capable of being served thereby.

BACKGROUND OF THE INVENTION

1. Field of the Invention

The fields of the invention reside in biochemistry and in pharmacology. This invention relates to the synthesis and the therapeutic uses of various dosage forms comprised of D,α-tocopherol nicotinate and their uses as nutritional supplements and therapeutic agents.

2. Description of the Prior Art

D,α-tocopherol (Vitamin E, DAT)

Dextro and levo stereoisomeric forms of a-tocopherol exist, but the dextro form is the most physiologically active and the most nutritionally useful.

The lipid soluble, free oxygen radical scavenger (DAT) or vitamin E has a variety of antioxidant activities which include among others: promotion of the Ach/cAMP synthesis of nitric oxide (NO), decomposition of fatty acid hydroperoxides and hydrogen peroxides, maintenance of cell membrane stability, prevention of DNA strand breakage, improvement in the uptake of glutamate by synaptosomes at neural junctions and the suppression of oxidative conversion of low density lipids. These pluralistic activities have been demonstrated in several ways and confirm its preventive role in the development of some human diseases:

1. Vascular oxidative stress brought about by superoxide radicals and oxidized low-density lipoproteins (oxLDL) are major factors contributing to decreased NO-dependent vasodilator functions in hypercholesterolemia and atherosclerosis. DAT antagonizes the oxLDL-related events in atherogenesis. DAT is generally regarded as the most important lipid-soluble, chain-breaking antioxidant in human plasma.
2. There is epidemiological evidence that suggests that the incidence of human cardiovascular disease is lowered in populations having a high level of antioxidants, such as vitamin E, in their diet, or who have enhanced their level of intake of this vitamin by taking dietary supplements. The antioxidant defense of elderly patients is improved even with low doses of supplemental vitamin E.
3. The addition of vitamin E in doses of 400 mg once a day, orally for 4 weeks significantly reduces malonyldialdehyde and superoxide anion levels and produces an elevation of antioxidant enzymes. After vitamin E supplementation, there is a normalization of the indices of oxidative stress following heart failure; this is especially true for catalase, glutathione reductase and superoxide dismutase. Following supplementation with DAT, glutathione peroxidase (GSHPx) activities (necessary for the decomposition of fatty acid hydroperoxides) increase as much as twofold.
4. In patients with active variant angina who continue to have anginal attacks in spite of receiving calcium channel blockers, the addition of vitamin E significantly elevates plasma alpha-tocopherol levels and inhibits the further occurrence of angina. Plasma vitamin E levels are significantly lower in patients with active variant angina than in subjects without coronary spasm, suggesting an association between vitamin E deficiency and persistent coronary artery spasm.
5. Reactive oxygen species (ROS) produced by cells of the arterial wall may cause oxidative damage to cellular components altering endothelial cell function. Changes in endothelial cell function play a key role in the pathogenesis of atherosclerosis. However, human aortic endothelial cells pre-incubated with vitamin E demonstrate a dose-dependent increase in resistance to oxidative stress and increased cell viability from 37% to 85%.
6. Vitamin E has an inhibitory effect on the oxLDL-induced production of vascular endothelial adhesion molecules and upon the adhesion of monocytes to vascular endothelium; this functional alteration may take place via DAT's antioxidant abilities and/or its direct regulatory effect on sICAM-1 expression. The rheological properties of blood and red cell deformability may be improved by DAT. This can be attributed to reduced lipid peroxidation stress on the membrane envelop of red blood cells. Supplementation with vitamin E may be useful in slowing the clinical deteriorations associated with microangiopathic conditions in diabetes mellitus Type 2. All of these activities reduce the development of conditions of risk associated with vasoconstriction.
7. Tobacco-specific nitrosamines are common metabolites of nicotine and are major carcinogens in cigarette smoke. Conditions of chronic inflammation may enhance or promote the carcinogenic effect of these nitrosamines through the generation of toxic oxygen radicals, which cause a significant increase in DNA strand breakage. In vitro pre-treatment of these cells with vitamin E provides significant protection against the induction of DNA damage.
8. More alpha-tocopherol derived from the synaptosomes of older rats is oxidized than that derived from the synaptosomes younger rats. These older animals may be more susceptible to conditions of neural glutamate excitotoxicity because: a) synaptosomal reuptake of glutamate is less efficient and, b) oxidative stress induced by various agents including glutamate may be higher in older animals. Improving synaptosomal levels of alpha-tocopherol in the elderly provides protection from neural excitotoxicity; this may be particularly important in conditions of cardiac ischemia and irregularities.

Nicotinamide, Niacin, Nicotinate (NIC)

The water-soluble vitamin nicotinamide, or niacin, has established itself as a supplement appropriate for reducing plasma oxLDL in patients at risk of atherosclerosis or vasoconstriction and their attendant clinical diseases. It also has the additional functional benefit of decreasing plasma fibrinogen levels and stimulating fibrinolysis, thus reducing the risk of thrombosis and embolism. An additional plus for these patients is the apparent improvement in cardiac glucose utilization that occurs with nicotinic acid supplementation and the suggestion that there is a concurrent improvement in zinc ($Zn^{+2}$) uptake. However, when nicotinamide is used simultaneously with pharmacological levels of lipid-reducing statins, there is concern for hepatic health.

1. Niacin supplementation decreases plasma fibrinogen and LDL cholesterol in subjects with peripheral vascular disease: in general, changes in fibrinogen levels seem to be quite closely correlated with niacin-induced reductions in LDL cholesterol.
2. Nicotinic acid in gram doses decreases cholesterol and triglyceride concentrations in plasma. At the same time it is lowering the triglyceride levels it is also reducing the fibrinogen concentration in plasma and stimulates fibrinolysis.
3. As measured by uptake of 18F-fluorodeoxyglucose and PET imaging, niacin treatment of normal volunteers is associated with a two- to three-fold increase in exogenous glucose utilization by the heart; a significant decrease in fatty acid levels is associated with these increases in myocardial glucose utilization rates.
4. Nicotinic acid and nicotinamide (at 1000 mg/kg) cause elevations in liver $NAD^+$; poly(ADP-ribose) is a homopolymer of ADP-ribose units synthesized from $NAD^-$ on nuclear acceptor proteins and is known to be involved in DNA repair. Nicotinamide treatment significantly elevates liver polyADP-ribose above control groups.
5. Nicotinic acid supplementation given to laboratory mice significantly increases $Zn^{+2}$ absorption—by 38.9% in fasting states and by 70.9% in postprandial conditions. Because of the important role of $Zn^{+2}$ in many nutritional functions, nicotinic acid supplementation, especially in the aged, is advisable.

SUMMARY OF THE INVENTION

Synthesis of D, alpha-tocopherol Nicotinate

The present invention comprises the compound of D,α-tocopherol nicotinate ($C_{35}H_{53}NO_3$). The present invention also includes the pharmaceutically acceptable salts of this compound such as the hydrochloride, hydrobromide and nitrate salts. This compound has been described as a racemic mixture in Japanese Patent 24,968 (1964) to Eisai Company. It was prepared by treating D,L,α-tocopherol with nicotinic acid chloride in pyridine. In the present invention, optically pure D,α-tocopherol is employed as the starting material to prepare D,α-tocopherol nicotinate according to the Eisai procedure as follows:

A solution of 34.6 grams of D,α-tocopherol in 100 mL of toluene is added to a solution of 13.6 g of nicotinic acid chloride hydrochloride (Aldrich Chemical Company) dissolved in 100 mL of pyridine/toluene (1:1). The reaction mixture is allowed to stand overnight and then diluted with another 100 mL of toluene. The resulting solution is washed with dilute 5% sodium bicarbonate solution and water, dried over sodium sulfate and evaporated to dryness under reduced pressure. The residue is dissolved in a 1:1 mixture of ethyl acetate-hexane and filtered through a column of 1 kg of neutral alumina and the product eluted with a mixture of ethyl acetate-hexane (1:1) and ethyl acetate. The fractions containing the product are combined, concentrated and recrystallized with acetone-hexane to give D,α-tocopherol nicotinate.

THERAPEUTIC APPLICATIONS

At present, patients or medical professionals who wish to use or recommend D,α-tocopherol and niacin, or nicotinic acid, must use each separately. Nothing is currently available which makes available, in a unified molecule, both biofactors. One result of the present situation is the use of self-prescribed and inappropriately high or low doses of either, or both, of the biofactors by unaware end users or medical practitioners. Because D,α-tocopherol and nicotinic acid have physiological behaviors which are at the same time complementary and additive, it seems appropriate to combine them into one complex both for efficiency and for safety: since the invention is carefully designed, it will provide to the user appropriate amounts of each biofactor which are therapeutically useful and safe. This is particularly important for users who also consume anti-lipid statins and who risk hepatic embarrassment when excessive niacin is also ingested. It should be noted that those users who require statins for the reduction of undesirably high levels of LDL cholesterol comprise the same group who benefit from nicotinic acid.

The present invention provides a compound of formula $C_{35}H_{53}NO_3$. Unlike the commonly available racemic mixtures of D,L,α-tocopherol and separate availability of various forms of niacin, the invention is a method for synthesizing and for using the more highly physiologically active and useful D,α-tocopherol nicotinate as a nutrient in a human by means of oral administration in various dosage forms. The compound may be in the form of a salt or a complex. The compound is preferably administered in an oral, total daily dosage of between about 50 mg and 1500 mg, excluding excipients.; however the most preferred oral daily dosage is between about 250 mg and 1000 mg, excluding excipients. Embodiments of the invention include administration in unit dosage forms that include tablets, capsules, powders, suspensions and liquids. Delivery vehicles of the invention contemplate among others, timed release, sustained release, controlled release or zero order release, in substantially homogenous or in coated bilayered release unit dosage forms with differential dissolution rates.

The present invention provides for the synthesis of D,α-tocopherol nicotinate compounds, which permits the unique therapeutic delivery of concurrent, pharmacologically appropriate dosage forms and amounts of D,α-tocopherol and nicotinate for the modification of conditions and functions associated with acute or chronic diseases involving dysfunctional vascular endothelium, vasoconstriction, excitotoxic neuronal damage and DNA strand breakage. Patients who smoke and patients with chronic glaucoma, macular degeneration, diabetes mellitus Type 1 or 2, systemic hypertension, peripheral vascular disease, coronary artery disease, cardiac irregularities, cerebral vascular disease, Alzheimer's disease or dyslipogenesis, among others, are contemplated by the invention.

DETAILED DESCRIPTION OF THE INVENTION AND PREFERRED EMBODIMENTS

All patents and published materials cited in this specification are incorporated herein by reference.

Definitions

All terms appearing in this specification and the appended claims are used in the same manner as commonly recognized among those skilled in the technology and terminology of pharmacology. These terms are therefore used in accordance with their conventional definitions, except as otherwise noted. Further clarifications of some of these terms as they apply specifically to this invention are offered below.

"Unit dosage form" refers to a composition intended for a single administration to treat a subject for the purpose of modifying an existing clinical condition or physiological function. Each unit dosage form typically comprises each of the active ingredients of this invention plus pharmaceutically acceptable excipients. Examples of unit dosage forms are individual tablets, individual capsules, bulk powders, and liquid solutions, emulsions or suspensions. Modification of the clinical condition or function may require periodic administration of unit dosage forms, for example: one unit dosage form two or more times a day, one with each meal, one every four hours or other interval, or only one per day. The expression "oral unit dosage form" indicates a unit dosage form designed to be taken orally.

An "active agent" or "active ingredient" is a component of a dosage form that performs a biological function when administered or induces or affects (enhances or inhibits) a physiological condition, process, or function in some manner. "Activity" is the ability to perform the function, or to induce or affect the process. Active agents and ingredients are distinguishable from excipients such as carriers, vehicles, diluents, lubricants, binders, and other formulating aids, and encapsulating or otherwise protective components.

"Delivery vehicle" is a composition, which comprises one or more active agents, and is designed to release the active agent in a particular fashion, either by immediately dispersing the agents in the digestive system, or by releasing the agents in a slow sustained fashion. The term encompasses porous microspheres, microcapsules, cross-linked porous beads, and liposomes that contain one or more active ingredients sequestered within internal cavities or porous spaces. The term also includes osmotic delivery systems, coated tablets or capsules that include nonporous microspheres, microcapsules, and liposomes, and active agents dispersed within polymeric matrices. A dosage form can include one or more delivery vehicles.

"Controlled" or "sustained" or "time release" delivery are equivalent terms that describe the type of active agent delivery that occurs when the active agent is released from a delivery vehicle at an ascertainable and manipulatable rate over a period of time, which is generally on the order of minutes, hours or days, typically ranging from about thirty minutes to about 3 days, rather than being dispersed immediately upon entry into the digestive tract or upon contact with gastric fluid. A controlled release rate can vary as a function of a multiplicity of factors. Factors influencing the rate of delivery in controlled release include the particle size, composition, porosity, charge structure, and degree of hydration of the delivery vehicle and the active ingredient(s), the acidity of the environment (either internal or external to the delivery vehicle), and the solubility of the active agent in the physiological environment, i.e., the particular location along the digestive tract.

The phrase "therapeutically effective amount" means an amount sufficient to produce a therapeutic result. Generally the therapeutic result is an objective or subjective improvement of a disease or condition, achieved by inducing or enhancing a physiological process, blocking or inhibiting a physiological process, or in general terms performing a biological function that helps in or contributes to the elimination or abatement of the disease or condition.

"Vasoconstriction" is the reduction of the cross section of a blood vessel lumen, inhibiting the free flow of blood through the vessel. Vasoconstriction can arise from platelet agglutination, acute or chronic contraction of vascular muscular layers, deposits on or in the lumen wall or from the thickening of the wall due to excessive growth or proliferation of one or more of the wall layers.

The phrase "substantially homogeneous," when used to describe a formulation (or portion of a formulation) that contains a combination of components, means that the components, although each may be in particle or powder form, are fully mixed so that the individual components are not divided into discrete layers or form concentration gradients within the formulation.

Solubility and Gastrointestinal Absorption Characteristics

Biomolecules are absorbed through the gastrointestinal epithelium by a variety of mechanisms; some passively according to concentration gradients, others require active transport by membrane-bound protein molecules that may be distributed differently along the course of the gastrointestinal tract and which may be more or less selective. Some gastrointestinal absorption of ions, heavy metals or biomolecules may occur by more than one mechanism.

The mucus layer covering the surface of the gastrointestinal tract may act as a barrier to drug absorption; therefore, the self-diffusion coefficients of drugs with different physicochemical properties in gastrointestinal mucus are important considerations. The most important physicochemical characteristic influencing the diffusion coefficient of smaller molecules through gastrointestinal mucous appears to be their lipophilicity; molecular size appears to have more influence for larger peptide drugs. Electrical charge has only a minor effect on the diffusion coefficients across the intestinal barrier.

a) D,α-tocopherol

| | |
|---|---|
| Absorption: | The gastrointestinal absorption of dietary DAT is bile salt dependent and therefore is somewhat also dependent upon the simultaneous digestion and absorption of fat. The presence of dietary taurine, involved in the conversion of cholic acid to dexycholic acid in the gut, enhances DAT absorption. In these |

-continued

| | |
|---|---|
| | respects DAT absorption may be similar to that of vitamin A and the site of major vitamin A absorption is the proximal small intestine. |
| Pharmacokinetics: | Evidence suggests that further uptake of the tocopherols, retinols, and carotenoids by the colonic mucosa occurs in the deep cryptal zone where actively proliferating cells extract these nutrients from the systemic circulation. | b) Nicotinate, Nicotinamide, Niacin

| | |
|---|---|
| Absorption: | Immediate release forms achieve higher plasma levels than sustained release forms. Formulations with high doses produce nonlinear kinetics, e.g., a 10-fold increase in the dose of standard nicotinamide, produces a 62-fold increase in the plasma concentration-time curves (AUC). |
| Pharmacokinetics: | In young adult men, there appear to be no significant differences in the kinetics of low dose standard nicotinamide (2.5 mg/kg) and low-dose, long acting nicotinamide (Enduramide) (6.7 mg/kg). Nonlinear kinetics have been found with both formulations at high doses, indicating high bioavailability. |

Composition, Formulations and Dosages

TABLE I

For otherwise healthy adults, Adequate Intake Values for Vitamin E (isomer is unspecified) and for niacin are currently set at modest levels within the range shown below as "Most Preferred". However, within the range designated below as "Preferred" the invention particularly contemplates usage in adults with significant risk of disease and is designed to provide either higher or lower levels, as might be necessary Daily Dosages in milligrams
D,α-Tocopherol Nicotinate

| Ranges in milligrams per day | Compound | Tocopherol | Nicotinate |
|---|---|---|---|
| Components for D,α-Tocopherol Nicotinate from Immediate Release Tablet | | | |
| Preferred | 67 | 40 | 10 |
| to | 2019 | 1200 | 293 |
| Most Preferred | 337 | 200 | 49 |
| to | 1346 | 800 | 195 |
| Components for D,α-Tocopherol Nicotinate from Sustained Release Tablet | | | |
| Preferred | 64 | 40 | 10 |
| to | 1904 | 1200 | 293 |
| Most Preferred | 317 | 200 | 49 |
| to | 1269 | 800 | 195 |

The slower, more sustained release of the active agents can be achieved by placing the active agents in one or more delivery vehicles that inherently retard the release rate. Examples of such delivery vehicles are polymeric matrices that maintain their structural integrity for a period of time prior to dissolving, or that resist dissolving in the stomach but are readily made available in the post-gastric environment by the alkalinity of the intestine, or by the action of metabolites and enzymes that are present only in the intestine. The preparation and use of polymeric matrices designed for sustained drug release is well known. Examples are disclosed in U.S. Pat. No. 5,238,714 (Aug. 24, 1993) to Wallace et al.; Bechted, W., *Radiology* 161: 601–604 (1986); and Tice et al., EPO 0302582, Feb. 8, 1989. Selection of the most appropriate polymeric matrix for a particular formulation can be governed by the intended use of the formulation. Preferred polymeric matrices are hydrophilic, water-swellable polymers such as hydroxymethylcellulose, hydroxypropylcellulose, hydroxyethylcellulose, hydroxymethylpropylcellulose, polyethylene oxide, and porous bioerodible particles prepared from alginate and chitosan that have been ionically crosslinked.

A delayed, post-gastric, prolonged release of the active ingredients in the small intestine (duodenum, ileum, jejunum) can also be achieved by encasing the active agents, or by encasing hydrophilic, water-swellable polymers containing the active agents, in an enteric (acid-resistant) film. One class of acid-resistant agents suitable for this purpose is that disclosed in Eury et al., U.S. Pat. No. 5,316,774 ("Blocked Polymeric Particles Having Internal Pore Networks for Delivering Active Substances to Selected Environments"). The formulations disclosed in this patent consist of porous particles whose pores contain an active ingredient and a polymer acting as a blocking agent that degrades and releases the active ingredient upon exposure to either low or high pH or to changes in ionic strength. The most effective enteric materials include polyacids having a $pK_a$ of from about 3 to 5. Examples of such materials are fatty acid mixtures, methacrylic acid polymers and copolymers, ethyl cellulose, and cellulose acetate phthalates. Specific examples are methacrylic acid copolymers sold under the name EUDRAGIT®, available from Rohm Tech, Inc., Maiden, Massachusetts, USA; and the cellulose acetate phthalate latex AQUATERIC®, available from FMC Corporation, New York, N.Y., USA, and similar products available from Eastman-Kodak Co., Rochester, N.Y., USA.

Acid-resistant films of these types are particularly useful in confining the release of magnesium lactate and magnesium citrate to the post-gastric environment. Acid-resistant films can be applied as coatings over individual particles of the components of the formulation, with the coated particles then optionally compressed into tablets. An acid-resistant film can also be applied as a layer encasing an entire tablet or a portion of a tablet where each tablet is a single unit dosage form.

The dosage forms of the invention optionally include one or more suitable and pharmaceutically acceptable excipients, such as ethyl cellulose, cellulose acetate phthalates, mannitol, lactose, starch, magnesium stearate, sodium saccharin, talcum, glucose, sucrose, carbonate, and the like. These excipients serve a variety of functions, as indicated above, as carriers, vehicles, diluents, binders, and other formulating aids. In general, the dosage forms of this invention include powders, liquid forms, tablets or capsules.

In certain embodiments of the invention, the dosage form is a substantially homogeneous single layer tablet that releases all of its components into the stomach upon ingestion.

In certain other embodiments of the invention, the dosage form is protected by an acid-resistant coating for release only in the intestine, and in a sustained-release manner over a period of time.

The dosage forms of this invention can be formulated for administration at rates of one or more unit dosage forms per day. Unit dosage forms to be taken three to four times per day for the single layer tablet and once or twice daily for the sustained release tablet are most preferred.

The following examples are offered for purposes of illustration only.

EXAMPLE 1

Immediate Release Tablet

Unit dosage forms to be taken three or four times per day for the single layer tablet are most preferred.

A single layer tablet, substantially homogenous in composition, which will disintegrate upon ingestion to provide simultaneous accessibility to all components, is prepared with the following composition:

TABLE II

Components for D,α-Tocopherol Nicotinate: Immediate Release Dosage Form

IMMEDIATE RELEASE

D,α-Tocopherol Nicotinate

| Ranges in milligrams per day | Compound | Tocopherol | Nicotinate |
|---|---|---|---|
| Preferred | 67 | 40 | 10 |
| to | 2019 | 1200 | 293 |
| Most Preferred | 337 | 200 | 49 |
| to | 1346 | 800 | 195 |

SINGLE LAYER UNIT DOSAGE FORM FOR: D,α-Tocopherol Nicotinate tabs / day: 3.00

TABLET WEIGHT: 230 mg / day: 690

FOR IMMEDIATE RELEASE IN THE STOMACH: 100% per day: Tocopherol 410 mg

| | | % of formula | milligrams | | | mg | mcg |
|---|---|---|---|---|---|---|---|
| $C_{35}H_{53}NO_3$ | D,α-Tocopherol Nicotinate | 73.88% | 509.81 | Toc excipients | Nicotinate | 100 | |
| $Mg(C_{18}H_{35}O_2)_2$ | Magnesium Stearate | 0.76% | 5.21 | Mag | Stearate | 5.0 | |
| ....... | Starch | 25.36% | 175.00 | | Starch (25%) | 175 | |

AQUEOUS FILM

Upon oral ingestion of the tablet, agents of the immediate release tablet dissolve rapidly in the stomach and are available for immediate absorption in the gastrointestinal tract.

EXAMPLE 2

Sustained Release Tablet

Unit dosage forms to be taken one to two times per day for the sustained release tablet are most preferred.

The next example illustrates a sustained release tablet, substantially homogenous in composition, with controlled release such that the tablet remains intact until reaching the intestine where it provides accessibility to all of its components in a sustained manner. The tablet is prepared with the following composition:

TABLE III

Components for D,α-Tocopherol Nicotinate: Sustained Release Dosage Form

SUSTAINED RELEASE

D,α-Tocopherol Nicotinate

| Ranges in milligrams per day | Compound | Tocopherol | Nicotinate |
|---|---|---|---|
| Preferred | 64 | 40 | 10 |
| to | 1904 | 1200 | 293 |
| Most Preferred | 317 | 200 | 49 |
| to | 1269 | 800 | 195 |

SINGLE LAYER UNIT DOSAGE FORM FOR: D,α-Tocopherol Nicotinate tabs / day: 1.00

TABLET WEIGHT: 651    mg / day: 651

FOR SUSTAINED RELEASE: 100% per day — Tocopherol 410 mg

| | % of formula | milligrams | | | mg | mcg |
|---|---|---|---|---|---|---|
| $C_{35}H_{53}NO_3$ D,α-Tocopherol Nicotinate | 78.35% | 509.81 | Toc Excipients | Nicotinate | 100 | |
| Mg $(C_{18}H_{35}O_2)_2$ Magnesium Stearate | 0.75% | 4.90 | Mag | Stearate | 4.7 | |
| ........ Polymer (H₂0 Sol, Cellulose) | 20.90% | 136.00 | | Polymer (20%) | 136 | |

ACID RESISTANT FILM

The polymer matrix of the controlled release tablet, having been given an enteric coating in the granulation process with EUDRAGIT, does not dissolve in the acid pH of the stomach, but remains intact until it passes to the upper part of the small intestine, where the enteric coating dissolves in the more alkaline environment of the intestine. The polymeric matrix then immediately begins to imbibe water from the intestinal fluid, forming a water-swollen gel. The agents incorporated into this layer are then available for intestinal absorption as they osmotically diffuse from the gel. The rate of diffusion of the agent is reasonably constant for the useful life of the matrix (approximately four hours), by which time the incorporated agent is finally depleted and the matrix disintegrates.

Methods of Administration and Types of Utility

The compositions and dosage forms of the invention are useful for modifying a variety of conditions or functions associated with endothelial dysfunction, dyslipogenesis, vasoconstriction, vascular insufficiency, neuronal excitotoxicity and various chronic diseases adversely impacted by these risk factors. The carefully chosen active ingredients of the invention act in a well-defined, uniquely efficient and complementary biochemical partnership to ensure that vascular risk factors are reduced. The resulting improvement in systemic, coronary, cerebral and ocular endothelial health maximizes the potential for success of current therapeutics and minimizes the potential that present treatment regimes will fail because of neglected, unrecognized or unappreciated vascular inadequacy. Patients most commonly first diagnosed with peripheral vascular disease, with glaucoma or macular degeneration, are also in an age group moving into an expanding physiological arena of widespread, aging, cellular inefficiencies. In addition, these patients may have accumulated several decades of cigarette smoking or exposure to other environmentally-induced DNA strand breakage. At the same time, these patients face a concomitant increasing incidence of associated chronic diseases (e.g., diabetes mellitus, hypertension, cerebral vascular disease, coronary artery disease, etc.). The invention will be beneficial to members of all of these categories.

We claim:

1. A process for the preparation of D,α-tocopherol nicotinate, comprising reacting optically pure D,α-tocopherol with a member selected from the group consisting of nicotinic acid chloride hydrochloride, nicotinic acid chloride hydrobromide, and nicotinic acid nitrate.

* * * * *